United States Patent [19]

Pittman et al.

[11] 3,998,620
[45] Dec. 21, 1976

[54] METHOD FOR CONTROLLED RELEASE OF FLUOROKETONES

[75] Inventors: Allen G. Pittman, El Cerrito; William L. Wasley, Berkeley, both of Calif.

[73] Assignee: The United States of America as represented by the Secretary of Agriculture, Washington, D.C.

[22] Filed: Apr. 9, 1970

[21] Appl. No.: 27,175

[52] U.S. Cl. .................... 71/85; 71/70; 71/103; 71/106; 71/107; 71/109; 71/112; 71/123; 424/78; 424/303; 424/308; 424/312; 424/313; 424/314; 424/331
[51] Int. Cl.² .................................. A01N 9/00
[58] Field of Search .................... 71/123, 85

[56] References Cited
UNITED STATES PATENTS

| | | | |
|---|---|---|---|
| 3,384,628 | 5/1968 | Pittman et al. | 260/89.5 H |
| 3,443,928 | 5/1969 | Batchelor | 71/123 |
| 3,676,469 | 7/1972 | Urry | 71/94 X |

*Primary Examiner*—Glennon H. Hollrah
*Attorney, Agent, or Firm*—M. Howard Silverstein; William Takacs

[57] ABSTRACT

A precursor polymer is provided which affords slowly available herbicidal ketones of the formula

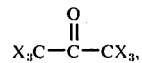

wherein the X terms are chlorine, fluorine or mixtures thereof.

6 Claims, No Drawings

METHOD FOR CONTROLLED RELEASE OF FLUOROKETONES

A non-exclusive, irrevocable, royalty-free license in the invention herein described, throughout the world for all purposes of the United States Government, with the power to grant sublicenses for such purposes, is hereby granted to the Government of the United States of America.

This invention relates to and has among its objects the provision of novel methods for releasing fluoroketones in various substrates, such as plants and soils, whereby to obtain the biological effects of such fluoroketones over a period of time from a single application of a precursor agent. Further objects of the invention will be evident from the following description wherein parts and percentages are by weight unless otherwise specified.

In U.S. Pat. No. 3,443,928 it is disclosed that various fluorinated ketones, typically hexafluoro-acetone, exhibit herbicidal action and may be applied, for example, to potato plants to kill the vegetative portion (vines) of the plants. It has also been reported that these fluoro-ketones are useful as defoliants, fungicides, nematocides, insecticides, etc. and for such purposes are applied to soils, plants, etc.

One of the problems in the use of these fluoro-ketones lies in their fugacity. Many of the compounds in question are gases or volatile liquids so that they are dissipated soon after application.

A primary object of the invention is to obviate the problem outlined above. In accordance with the invention certain agents (as hereinafter described) are applied to soils plants, or other substrates. These agents exhibit a relatively low volatility per se; however, under the influence of moisture these agents undergo a special type of cleavage resulting in the formation of a fluorinated ketone. This decomposition takes place at a slow rate so that the effective agent —the fluoro-ketone—is released over a substantial period of time. In effect, therefore, the fugacity of the fluorinated ketone is offset by providing it in increments over a period of time, yet by a single application of the precursor agent.

Among the agents used in accordance with the invention are esters of the following structure

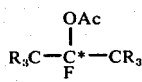
I.

wherein each R is a member of the group consisting of hydrogen, halogen, alkyl, haloalkyl, cycloalkyl, and halocycloalkyl, wherein at least two of the R's are fluorine, and wherein Ac is the acyl radical of an organic acid.

When these esters are exposed to moisture (as is the case when they are applied to soil, plants, or other moist substances), there occurs at a slow rate certain reactions centered about the alpha carbon atom (the one designated by an asterisk in Formula I) whereby the ester group is split off together with the fluorine atom which had occupied the alpha carbon position. The net result is the formation of a fluoro-ketone as illustrated below:

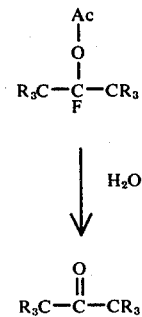

(By-products of the reaction are

and/or HF + HOAc, depending on the individual circumstances.)

Depending on the amount of moisture available, the released ketone may form a hydrate. This is of no particular consequence since the active component of the hydrate remains the ketone.

The agents of the invention are disclosed in our U.S. Pat. No. 3,384,628 (and the divisions thereof: U.S. Pat. Nos. 3,419,602, 3,465,050, 3,479,214, and pending application Ser. No. 826,655, filed May 21, 1969 now U.S. Pat. No. 3,637,791) and may be prepared by the procedure disclosed therein. This involves reacting the appropriate ketone with an alkali metal fluoride, then reacting the resulting intermediate with an acyl halide.

Examples of agents in accordance with the invention are listed below by way of illustration and not limitation.

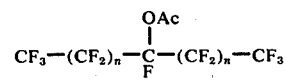

wherein each n is 0 to 10

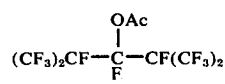

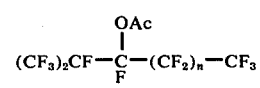

wherein n is 0 to 10

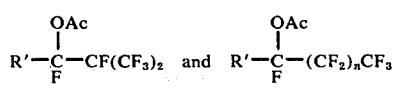

wherein R' is a perfluorocycloalkyl radical such as heptafluorocyclobutyl, and n is 0 to 10

wherein n is 3 to 10

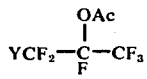

wherein Y is Cl, Br, or I, this being applicable to the following five formulas

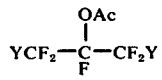

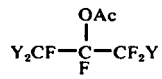

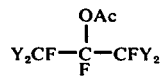

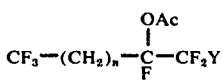

wherein n is 0 to 18

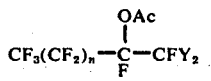

wherein n is 0 to 18

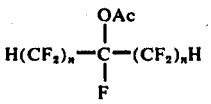

wherein each n is 1 to 18

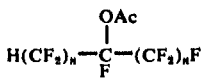

wherein each n is 1 to 18

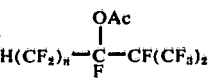

wherein each n is 1 to 18

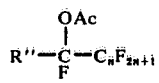

wherein R″ represents an alkyl group 1 to 18 carbon atoms, or a cycloalkyl group such as cyclopropyl, cyclobutyl, or cyclohexyl, and n is 1 to 18.

Also included in the broad scope of the invention are diesters, the following being typical of this category:

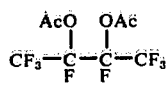

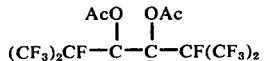

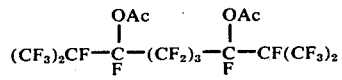

Among the preferred esters are those of the structures:

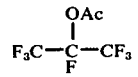

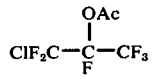

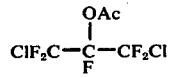

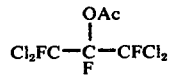

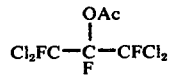

The acyl moiety of the esters may be varied very widely since the function thereof is primarily to decrease volatility. They (the acyl moieties) are not intended to contribute materially to the biological activity of the ester, although it is within the broad compass of the invention that they may be provided with a particular structure to supplement the activity of the released ketone. Accordingly, the esters may be derived from any of the following illustrative examples of acids: Aliphatic carboxylic acids such as acetic, propionic, butyric, hexanoic, lauric, and others of the series $C_nH_{2n+1}COOH$ wherein n is 0 to 20. Unsaturated aliphatic acids such as acrylic, methacrylic, or others of the general formula $CH_2=C(R)—COOH$, wherein R is H or a lower alkyl radical. Aromatic acids such as benzoic, toluic, naphthoic, anisoic, dodecylbenzoic, parachlorobenzoic, nitrobenzoic, 2,4-dichlorobenzoic, etc. Fluorinated acids such as those of the type $CF_3—(CF_2)_n—COOH$ wherein n is 0 to 18. Other carboxylic acids such as phenylacetic, ethoxyacetic, oleic, linoleic, linolenic, recinoleic, crotonic, hexahydrobenzoic, chloroacetic, cinnamic, phenoxyacetic, etc. Aromatic sulphonic acids such as benzene, toluene, xylene, naphthalene, anisole, phenetole, dodecylbenzene, nitrobenzene, parachlorobenzene, 2,4dichlorobenzene, α-toluene, etc. sulphonic acids. Aliphatic sulphonic acids, for example, compounds of the type $CH_3—(CH_2)_n—SO_3H$ wherein n is 0 to 18. Fluorinated aliphatic sulphinic acids, for example, compounds of the type $CF_3—(CF_2)_n—SO_3H$ wherein n is 0 to 18. Unsaturated sulphonic acids such as compounds of the type $CH_2=C(R)—SO_3H$ wherein R is H or lower alkyl. Other sulphonic acids such as cyclohexane and benzyl sulphonic acids. Although it is generally preferred to use esters of monofunctional acids, it is within the broad ambit of the invention to provide esters of polyfunctional acids such as maleic, malonic, succinic, adipic, itaconic, phthalic, isophthalic, terephthalic, benzene di-sulphonic, and the like, Also included are esters of organic carbonic acids, for example, esters which may be considered as derived from the following acids (without implying that such acids necessarily exist since the esters are actually produced from corresponding halides):

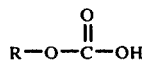

wherein R is an alkyl radical containing 1 to 18 carbon atoms, or an aryl radical such as phenyl, tolyl, xylyl, naphthyl, etc., or a fluorinated radical such as $HCF_2-(CF_2)_n-CH_2-$ or $CF_3-(CF_2)_n-CH_2-$, wherein n is 0 to 18.

The esters derived from unsaturated acids such as acrylic and methacrylic acids are polymerizable and such polymers may be prepared as disclosed in our U.S. Pat. No. 3,384,628. These polymers are included among the agents of the invention as they release the fluorinated ketone in the same manner as described above in connection with the monomeric esters. The polymers contain recurring units of the structure

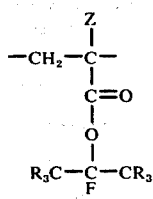

wherein Z is H or $CH_3$, and R is as defined in Formula I.

The aforesaid acrylates and methacrylates may be homopolymerized or they may be copolymerized with polymerizable monomers which do not contain fluorine, for example, methyl methacrylate or other alkyl acrylates or methacrylates, styrene, butadiene, vinyl acetate or chloride, acrylonitrile, acrylamide, and the like. Such copolymers are especially desirable where it is desired to form an agent of modified physical properties, for example, as to hardness, insolubility or solubility, permeability, etc.

The agents of the invention are applied to the locus to be treated in the same manner as one would apply other herbicides or defoliants; for example, they are applied by spraying or dusting the agent on the locus. The agent is preferably admixed with or dispersed in a carrier. The carrier may be a liquid such as water or an organic solvent such as a petroleum hydrocarbon distillate, benzene, carbon tetrachloride, benzotrifluoride, etc. A preferred technique is to emulsify the agent in water with the aid of a conventional emulsifying agent. Alternatively, the carrier may be a finely-divided solid such as talc, diatomaceous earth, wood flour, vermiculite, or finely-ground agricultural by-products such as nut shells, fruit pits, corn cobs, etc. For the desired release of the fluoro-ketone, it is essential that the treated locus be maintained in a moist condition. Thus, if the agents are applied in an arid location (as in application to shrubs in desert-type range lands), it may be necessary to apply moisture, as by spraying, to the treated locus. Normally, however, deliberate moistening is not required as there is sufficient moisture in the plants or soils to which the agents are applied and in the atmosphere about them. However, even in these cases, water may be deliberately applied if it is desired to ensure and/or expedite release of the fluoro-ketone. In herbicidal applications the agents of the invention are directly applied to the unwanted plants or to the soil near them. For such applications as destroying nematodes or insects in the soil they may be applied to the surface of the soil, or more preferably incorporated into the soil as by spraying them on the soil while concomitantly applying raking, plowing, harrowing, or similar mechanical action to mix the agent with the soil.

The invention is further demonstrated by the following illustrative examples.

EXAMPLE 1

Beans (Tendergreen variety) were planted in parallel rows about 5 inches apart. When the plants had grown to a height of about 6 inches and had several well developed leaves, the following experiments were carried out.

The plants in the first row were retained as untreated controls. The plants in the second row were sprayed with a blank emulsion, that is, one without any fluoro-polymer. The plants in the third and fourth rows were sprayed with an aqueous emulsion of 5 percent of the homopolymer of heptafluoroisopropyl acrylate (prepared as in Example 2 in U.S. Pat. No. 3,384,628), emulsified with the aid of 0.2 percent of a conventional emulsifier (Igepal DM 710).

The soil about the plants was watered from time to time to keep it moist. Two weeks after the treatment all the plants in the first row (controls) and all the plants in the second row (treated with blank emulsion) were healthy and none had lost any leaves. By this time, however, at least two-thirds of the leaves of the plants in the third and fourth rows had withered and fallen off, and the remaining leaves dropped off before the 17th day following the treatment. The bare stems of the treated plants withered and died within a few days after the last leaves had fallen off. The plants in the first two rows continued to grow and remained healthy throughout the experiment.

The foregoing experiment was repeated using a 5 percent aqueous emulsion of β-chloro-hexafluoroisopropyl stearate with results similar to those described above.

EXAMPLE 2

Samples of several polymers (identified below) were placed in loosely-stoppered vials so that they were exposed to atmospheric moisture. The samples were allowed to stand for several days at room temperature, and at intervals samples of head-space gas in each vial were analyzed by I.R. spectrum. This analysis showed that fluoro-ketones were gradually released into the head-space of each vial. The polymers used and the ketone found in the gas phase above each are tabulated below:

| Polymer | Ketone in gas phase |
| --- | --- |
| Poly(heptafluoroisopropyl acrylate) | $CF_3-CO-CF_3$ |
| Poly(heptafluoroisopropyl methacrylate) | " |
| Poly(β-chloro-hexafluoroisopropyl acrylate) | $ClCF_2-CO-CF_3$ |
| Poly(β-chloro-hexafluoroisopropyl methacrylate) | " |
| Poly(β,β'-dichloro-pentafluoroisopropyl acrylate) | $ClCF_2-CO-CF_2Cl$ |

-continued

| Polymer | Ketone in gas phase |
|---|---|
| Poly(β,β'-dichloro-pentafluoroisopropyl methacrylate) | " |

Analysis of the polymer materials from time to time using the IR technique also showed the gradual formation of polyacryloyl (or polymethacryoyl) fluoride, HF, and eventually IR bands characteristic of the COOH group.

Having thus described the invention, what is claimed is:

1. A method for gradually releasing a fluoro-ketone in plants or soils which comprises
   a. applying to the plant or soil a polymer containing recurring units of the structure

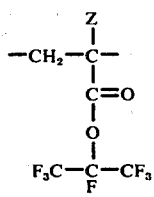

wherein Z is a member of the group consisting of H and CH$_3$, and
   b. maintaining the treated plant or soil in a moist condition whereby gradual cleavage of the polymer occurs with gradual release of a fluoro-ketone of the structure

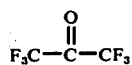

2. The method of claim 1 wherein the polymer is applied in an amount to provide a herbicidally-effective amount of the fluoro-ketone.

3. A method for gradually releasing a fluoro-ketone in plants or soils which comprises
   a. applying to the plant or soil a polymer containing recurring units of the structure

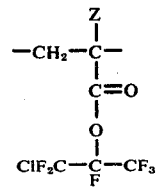

wherein Z is a member of the group consisting of H and CH$_3$, and
   b. maintaining the treated plant or soil in a moist condition whereby gradual cleavage of the polymer occurs with gradual release of a fluoro-ketone of the structure

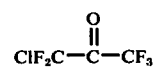

4. The method of claim 3 wherein the polymer is applied in an amount to provide a herbicidally-effective amount of the fluoro-ketone.

5. A method for gradually releasing a fluoro-ketone in plants or soils which comprises
   a. applying to the plant or soil a polymer containing recurring units of the structure

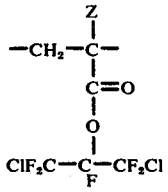

wherein Z is a member of the group consisting of H and CH$_3$, and
   b. maintaining the treated plant or soil in a moist condition whereby gradual cleavage of the polymer occurs with gradual release of a fluoro-ketone of the structure

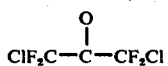

6. The method of claim 5 wherein the polymer is applied in an amount to provide a herbicidally-effective amount of the fluoro-ketone.

* * * * *